(12) United States Patent
Williams et al.

(10) Patent No.: US 7,764,370 B2
(45) Date of Patent: Jul. 27, 2010

(54) SYSTEM AND METHOD TO ZERO CHAMBERS IN A SURGICAL CASSETTE

(75) Inventors: David Lloyd Williams, Newport Beach, CA (US); Shawn X. Gao, Irvine, CA (US); David M. Domash, Irvine, CA (US); Nader Nazarifar, Laguna Niguel, CA (US)

(73) Assignee: Alcon, Inc., Hunenberg (CH)

( * ) Notice: Subject to any disclaimer, the term of this patent is extended or adjusted under 35 U.S.C. 154(b) by 1062 days.

(21) Appl. No.: 11/479,669

(22) Filed: Jun. 30, 2006

(65) Prior Publication Data

US 2008/0000485 A1 Jan. 3, 2008

(51) Int. Cl.
*G01N 1/10* (2006.01)

(52) U.S. Cl. ...................................... 356/246

(58) Field of Classification Search ............. 356/39, 356/246, 432–436, 440, 445, 448
See application file for complete search history.

(56) References Cited

U.S. PATENT DOCUMENTS

| 4,395,258 A | 7/1983 | Wang et al. |
| 4,493,695 A | 1/1985 | Cook |
| 4,627,833 A | 12/1986 | Cook |
| 4,713,051 A | 12/1987 | Steppe |
| 4,758,238 A | 7/1988 | Sundblom |
| 4,790,816 A | 12/1988 | Sundblom |
| 4,798,850 A | 1/1989 | Brown |
| 6,036,458 A | 3/2000 | Cole |
| 6,059,544 A | 5/2000 | Jung |
| 6,267,956 B1 | 7/2001 | Gomes |
| 6,293,926 B1 | 9/2001 | Sorensen |
| 6,364,342 B1 | 4/2002 | Kim |
| 2001/0016711 A1 | 8/2001 | Sorensen |
| 2003/0202894 A1 | 10/2003 | Leukanech |
| 2003/0204172 A1 | 10/2003 | Steppe |
| 2003/0225363 A1 | 12/2003 | Gordon |
| 2004/0074281 A1 | 4/2004 | Lobdell et al. |
| 2004/0106915 A1 | 6/2004 | Thoe |
| 2004/0253129 A1 | 12/2004 | Sorensen |
| 2005/0065462 A1 | 3/2005 | Nazarifar |
| 2005/0186098 A1 | 8/2005 | Davis |
| 2005/0234395 A1 | 10/2005 | Mackool |
| 2005/0285025 A1 | 12/2005 | Boukhny et al. |
| 2007/0073234 A1* | 3/2007 | Nazarifar et al. ............. 604/151 |
| 2007/0248477 A1* | 10/2007 | Nazarifar et al. ......... 417/477.2 |

* cited by examiner

*Primary Examiner*—Tarifur Chowdhury
*Assistant Examiner*—Jonathon D Cook
(74) *Attorney, Agent, or Firm*—Jonathan E. Prejean (57) ABSTRACT

Embodiments of the present invention provide a system and method for determining the location of the bottom of a fluid chamber in a surgical cassette to calibrate the surgical system. According to one embodiment, the surgical cassette is shaped to allow light from a light source to pass unobstructed to a linear sensor array in an area that is a known distance from the bottom of a fluid chamber. Light rays intersected by solid cassette material, on the other hand, will insufficiently illuminate the linear sensor array. Because the slot is a known distance from the bottom of the chamber, the location of the bottom of the chamber can be determined by determining the transition between illuminated and insufficiently illuminated portions of the linear sensor array.

8 Claims, 11 Drawing Sheets

SYSTEM AND METHOD TO ZERO CHAMBERS IN A SURGICAL CASSETTE

TECHNICAL FIELD OF THE INVENTION

The present invention relates to surgical system and methods. More particularly, the present invention relates to a system for zeroing chambers in a surgical cassette.

BACKGROUND OF THE INVENTION

The human eye can suffer a number of maladies causing mild deterioration to complete loss of vision. While contact lenses and eyeglasses can compensate for some ailments, ophthalmic surgery is required for others. Generally, ophthalmic surgery is classified into posterior segment procedures, such as vitreoretinal surgery, and anterior segment procedures, such as cataract surgery. More recently, combined anterior and posterior segment procedures have been developed.

The surgical instrumentation used for ophthalmic surgery can be specialized for anterior segment procedures or posterior segment procedures or support both. In any case, the surgical instrumentation often requires the use of associated consumables such as surgical cassettes, fluid bags, tubing, hand piece tips and other consumables.

A surgical cassette can provide a variety of functions depending on the procedure and surgical instrumentation. For example, surgical cassettes for cataract surgeries (e.g., phacoemulsification procedures) help manage irrigation and aspiration flows into and out of a surgical site. Surgical cassettes can also provide support for fluid bags, a manifold for directing vacuum/pressure to surgical instrumentation, and other functionality.

The fluid levels of an infusion/irrigation chamber and an aspiration chamber of a surgical cassette are measured to determine the amount of remaining fluid for procedure and fluid flow characteristics. To accurately determine the level of fluid in a chamber, the system employing the cassette should be calibrated to determine when the cassette is empty. Therefore, a method of zeroing a cassette chamber is needed.

SUMMARY OF THE INVENTION

Embodiments of the present invention provide an apparatus and method for zeroing chambers of a surgical cassette. One embodiment of the present invention includes a surgical system comprising a surgical cassette and a surgical console. The surgical cassette can be at least partially formed of a cassette material defining a chamber and comprising a first wall (for example, a console facing wall), a second wall (for example a side wall) and a zeroing feature a known distance below a bottom surface of the chamber. The console can include a cassette receiver to receive the surgical cassette, a sensor array and a plurality of light sources. The sensor array can have a plurality of vertically arranged portions to receive light and generate an output that indicates an illumination amount of each of the vertically arranged portions. The plurality of vertically arranged light sources can project light with at least one of the plurality of light sources positioned to project a light ray along a transmission path to the sensor array via the zeroing feature and at least another one of the plurality of light sources positioned to project a light ray along a transmission path intersected by cassette material. The system can further comprise a controller, which can be part of the console, that is operable to determine a vertical location of an upper edge of the zeroing feature based on the output of the linear sensor array and determine a vertical location of the bottom surface of the chamber based on the vertical location of the upper edge of the zeroing feature and the known distance.

Another embodiment of the present invention can include a surgical cassette defining a chamber having a bottom surface, the surgical cassette comprising a side wall, a surgical console facing wall and a shaped portion to allow light projected at the surgical console facing wall of the surgical cassette to pass unobstructed past the side wall of the cassette. The edge of the shaped portion can be a known distance from the bottom surface of the chamber.

Yet another embodiment of the present invention includes a method of determining the vertical location of a bottom surface of a chamber in a surgical cassette. The method can comprise emitting a plurality of light beams at a surgical cassette along parallel vertically spaced transmission paths. At least a portion of the plurality of light beams are directed at a portion of the surgical cassette shaped to allow that portion of the light beams to travel unobstructed to a linear sensor array. The method can further comprise detecting the illumination pattern of the linear sensor array by the plurality of light beams and determining the vertical location of the bottom surface of the chamber based on the illumination pattern.

Embodiments of the present invention provide an advantage by providing a mechanism to indirectly measure the locations of the bottoms of cassette chambers with a high degree of confidence.

Embodiments of the present invention provide another advantage in that the locations of the bottoms of the cassette chambers can be measured non-invasively.

BRIEF DESCRIPTION OF THE FIGURES

A more complete understanding of the present invention and the advantages thereof may be acquired by referring to the following description, taken in conjunction with the accompanying drawings in which like reference numbers indicate like features and wherein.

DETAILED DESCRIPTION

Preferred embodiments of the invention are illustrated in the FIGURES, like numerals being used to refer to like and corresponding parts of the various drawings.

As described below, a surgical system can use non-invasive level sensors to measure the levels of liquids in various chambers of a surgical cassette. The accurate measuring of these liquid levels may be necessary for some surgical procedures. Embodiments of the present invention provide a system and method for determining the location of the bottom of a fluid chamber in a surgical cassette to calibrate the surgical system. According to one embodiment, the surgical cassette is shaped to allow light from a light source to pass unobstructed to a linear sensor array in an area that is a known distance from the bottom of a fluid chamber. For example, the surgical cassette can include a slot that allows light to pass from the light source to the linear sensor array. The linear sensor array will register the light passing through the slot. Light rays intersected by solid cassette material, on the other hand, will insufficiently illuminate the linear sensor array. Because the slot is a known distance from the bottom of the chamber, the location of the bottom of the chamber can be determined by determining the transition between illuminated and insufficiently illuminated portions of the linear sensor array.

Additionally, the linear sensor array can register light that passes through air at the top of the chamber. Light encountering the area between the slot near the bottom of the chamber and the air at the top of the chamber can be reflected or refracted so that the linear sensor array registers an insufficient amount of light at corresponding portions. That is, the linear sensor array will detect light at that the top of the chamber (associated with air), detect light at the area associated with the slot, but detect an insufficient amount of light in-between. Because the transition between insufficiently illuminated and illuminated portions of the linear sensor array at the top of the chamber marks the liquid/air boundary in the chamber, the location of the top of the liquid column can be determined. The actual amount of liquid in the chamber can then be determined based on the difference between the location of the liquid/air interface and the location of the bottom of the chamber.

Figure 1:
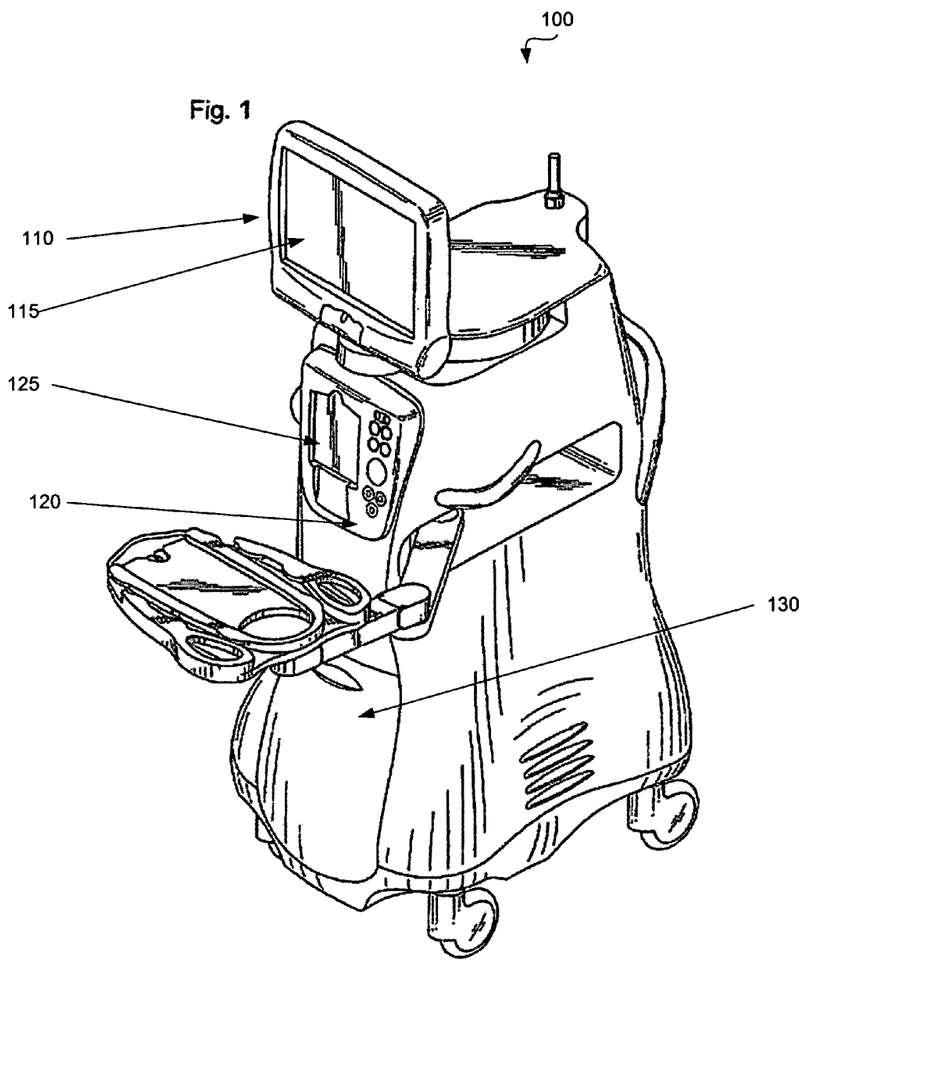
FIG. 1 is a diagrammatic representation of one embodiment of a surgical console in accordance with the teachings of this invention.

FIG. 1 is a diagrammatic representation of one embodiment of an ophthalmic surgical console 100 in which an embodiment of this invention can be implemented. Surgical console 100 can include a swivel monitor 110 that has touch screen 115. Swivel monitor 110 can be positioned in a variety of orientations for whomever needs to see touch screen 115. Swivel monitor 110 can swing from side to side, as well as rotate and tilt. Touch screen 115 provides a graphical user interface ("GUI") that allows a user to interact with console 100.

Surgical console 100 also includes a connection panel 120 used to connect various tools and consumables to surgical console 100. Connection panel 120 can include, for example, a coagulation connector, connectors for various hand pieces, and a cassette receiver 125. Surgical console 100 can also include a variety of user friendly features, such as a foot pedal control (e.g., stored behind panel 130) and other features.

In operation, a cassette (not shown) can be placed in cassette receiver 125. A clamp in surgical console 100 clamps the cassette in place to minimize movement of the cassette during use. The clamp can clamp the top and bottom of the cassette, the sides of the cassette or otherwise clamp the cassette.

Figure 2:
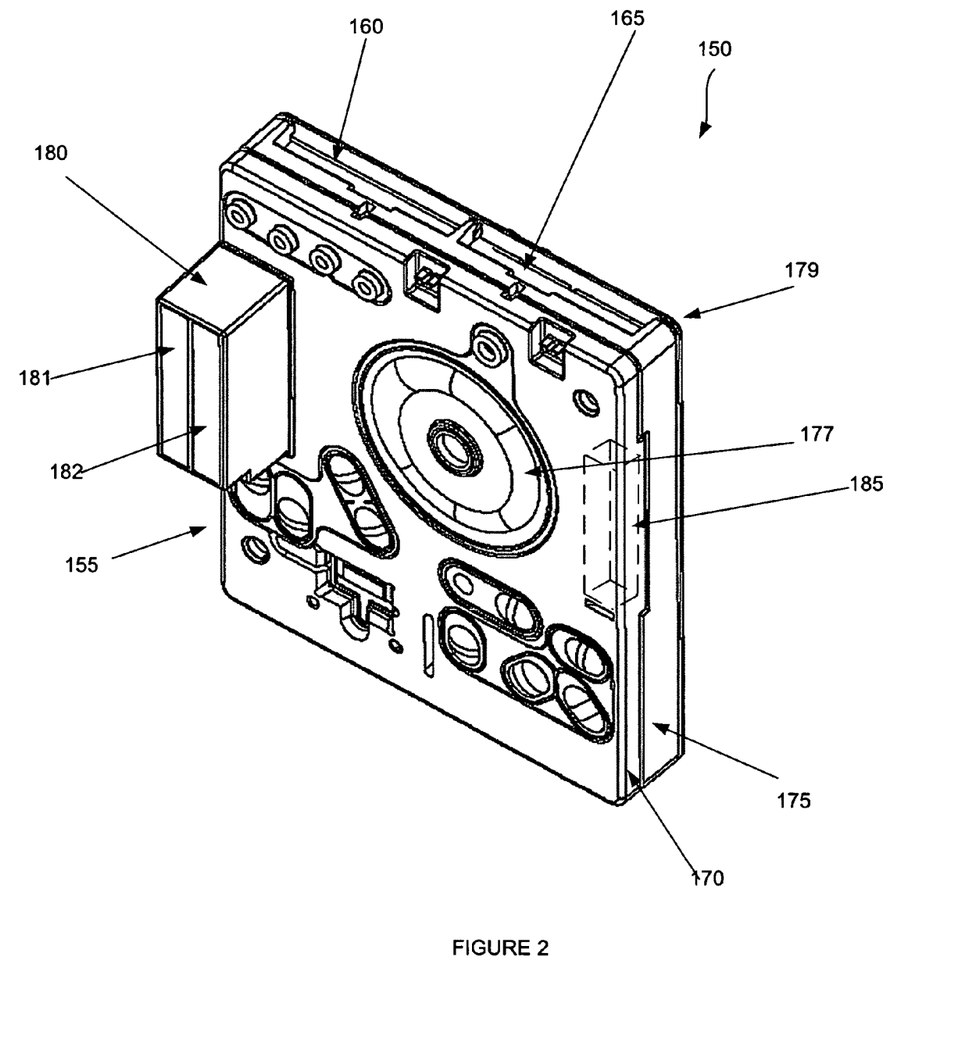
FIG. 2 is a diagrammatic representation of one embodiment of a surgical cassette in accordance with the teachings of this invention.

FIG. 2 is a diagrammatic representation of one embodiment of a surgical cassette 150. Cassette 150 can provide a closed system fluidic device that can be discarded following a surgical procedure. Cassette 150 can include a cassette body 155 and portions that interface with the clamp (e.g., indicated generally at clamping zones 160 and 165) projecting from the cassette body 155. Cassette 150 can be formed of ABS plastic or other suitable material. In the embodiment shown, cassette 150 is formed from three primary sections: an inner or surgical console interface section 170 that faces the surgical console when cassette 150 is inserted into surgical console 100, a middle section 175 and a cover plate 179. The various sections of cassette 150 can be coupled together via a press fit, interlocking tabs, chemical bonding, thermal bonding, mechanical fasteners or other attachment mechanism known in the art. In other embodiments, cassette 150 can be formed of a single piece or multiple pieces.

Surgical console interface section 170 can face the console during use and provide an interface for fluid flow channels (e.g., flow channel 177 for the peristaltic pump provided by an elastomeric pump membrane), valves (e.g., infusion/aspiration valves), and other features to manage fluid flow. Cassette 150 can also attach to a fluid bag (not shown) to collect fluids during a procedure.

Surgical cassette 150, according to various embodiments of the present invention, includes chambers to hold fluids for aspiration and infusion. For example, chamber cartridge 180 can include two infusion chambers 181/182. A third chamber 185 can be internal to cassette 150 on the opposite side of cassette 150 from chamber cartridge 180 (e.g., at the side of cassette 150 indicated by 190). According to one embodiment, the level of fluid in the chambers can be determined in a noninvasive manner. As described below, light can be projected into the chamber walls using vertically arranged light sources. Depending on the reflection or refraction of light at the chamber, a vertical sensor array will detect or not detect light at various points along the array's vertical axis. Based on the transition between illuminated and nonilluminated portions of the sensor array, the level of the fluid in the chamber can be detected.

Surgical cassette 150 can include features to allow light from the light source to pass to the linear sensor array at a location that is a predefined distance from the bottom of the chamber. For example, surgical cassette 150 can include a slot 186 beneath chamber 185 to allow light to pass to a linear sensor array. Chamber cartridge 180 can also include features (shown in FIG. 3B) below chambers 181/182 to allow light to pass to linear sensor arrays used for detecting the fluid level in chambers 181/182.

Figure 3A:
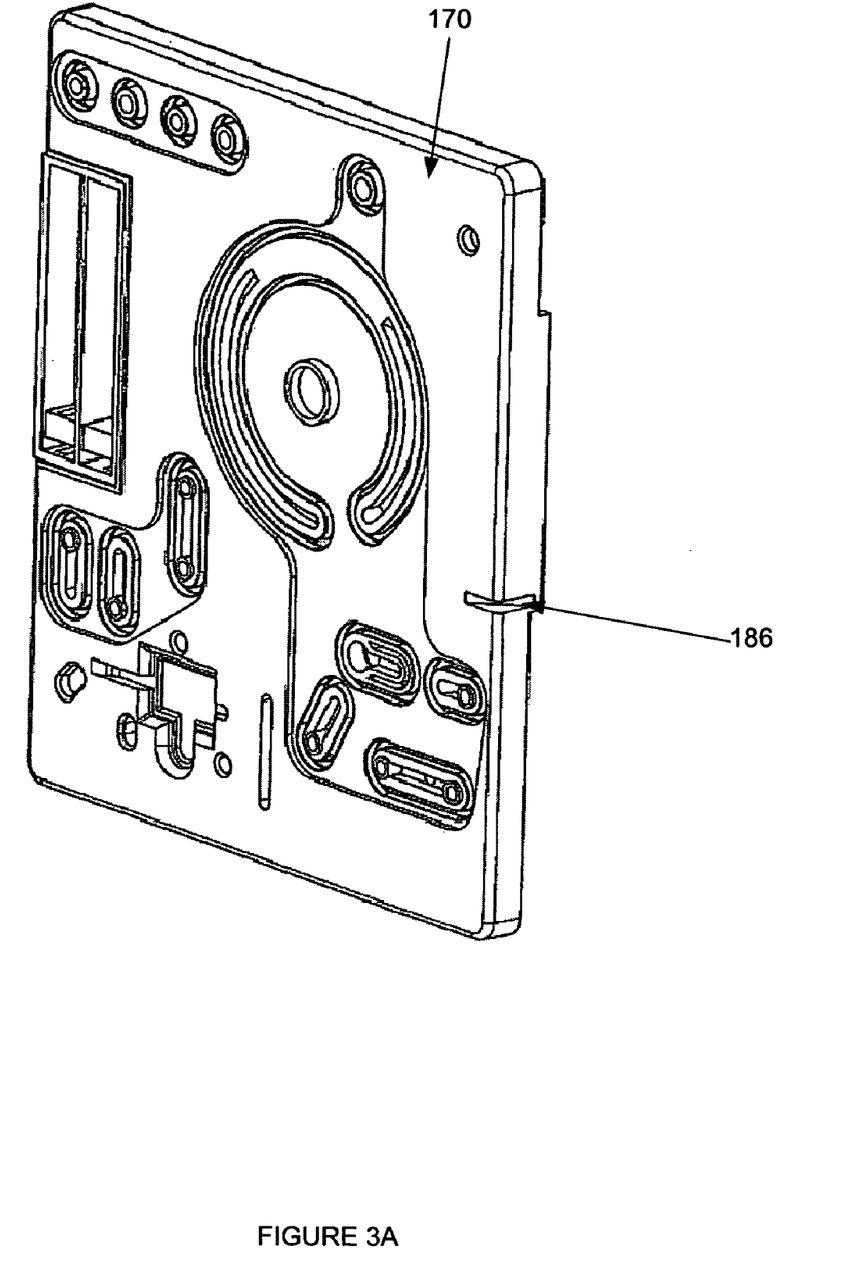
FIG. 3A is a diagrammatic representation of one embodiment of a chamber cartridge having zeroing features and FIG. 3B is a diagrammatic representation of one embodiment of a surgical cassette portion having a zeroing feature in accordance with the teachings of this invention.

FIG. 3A is a diagrammatic representation of one embodiment of surgical console interface section 170 of cassette 150. Surgical console interface section 170 can face the console during use and provide an interface for fluid flow channels, valves (e.g., irrigation/aspiration valves), pressure sensors and other features to manage fluid flow. Surgical console interface section 170 includes slot 186 a known distance d below the bottom surface of chamber 185 (shown in FIG. 2). This slot can allow light projected by a linear sensor array at the console facing wall to travel unobstructed past the side wall to a linear sensor array.

Figure 3B:
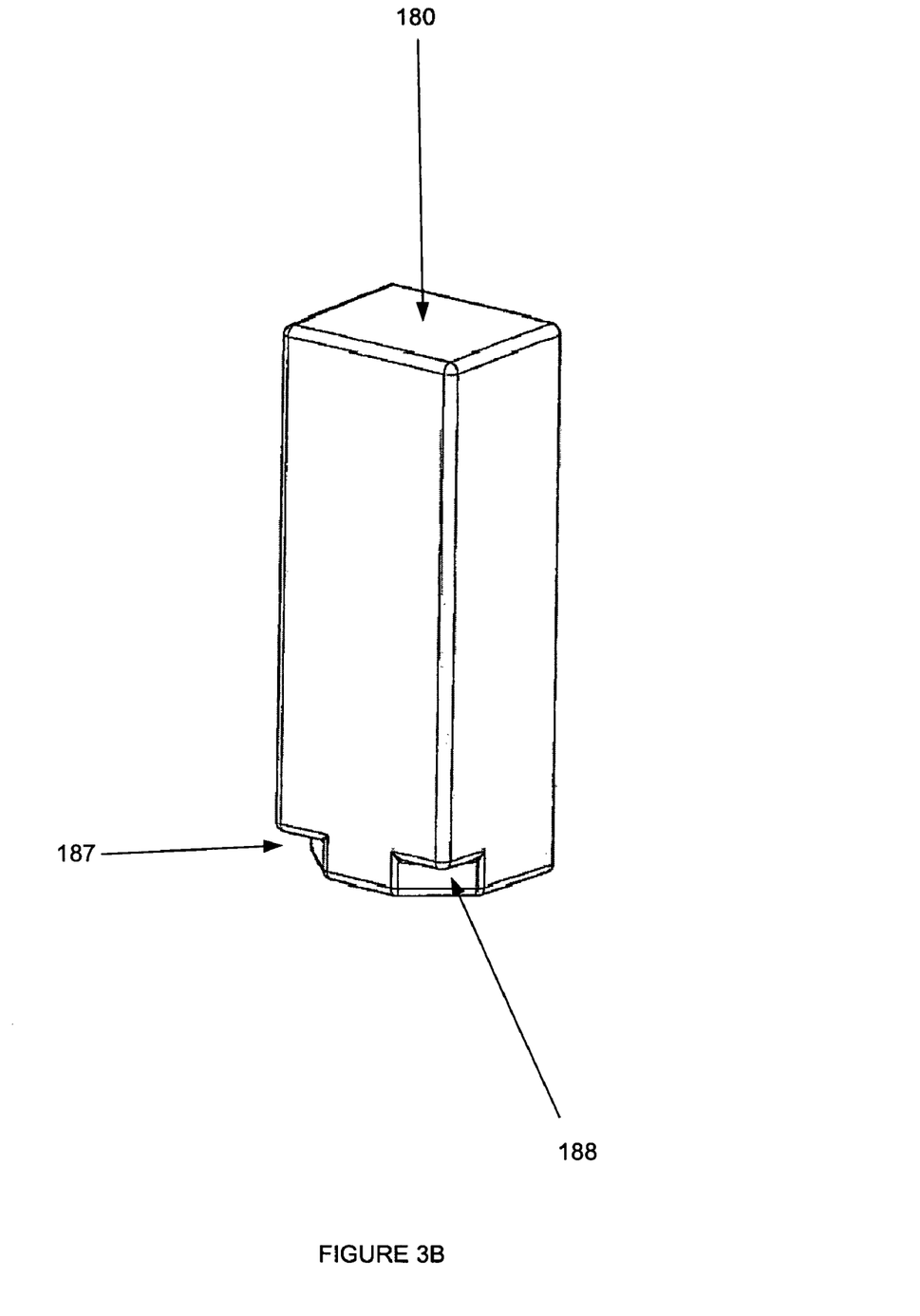

FIG. 3B is a diagrammatic representation of chamber cartridge 180 having chambers 181 and 182. Chamber cartridge 180 also includes features below each chamber to allow light to pass unobstructed from a light source to a linear sensor array. For example, chamber cartridge 180 includes zeroing features 187 and 188 below chambers 181/182 (shown in FIG. 2), respectively. Each of the zeroing features is shaped to allow light projected at console facing wall 189 by a linear light source to pass unobstructed past the sidewalls of cartridge 180 to linear sensors.

Figure 4:
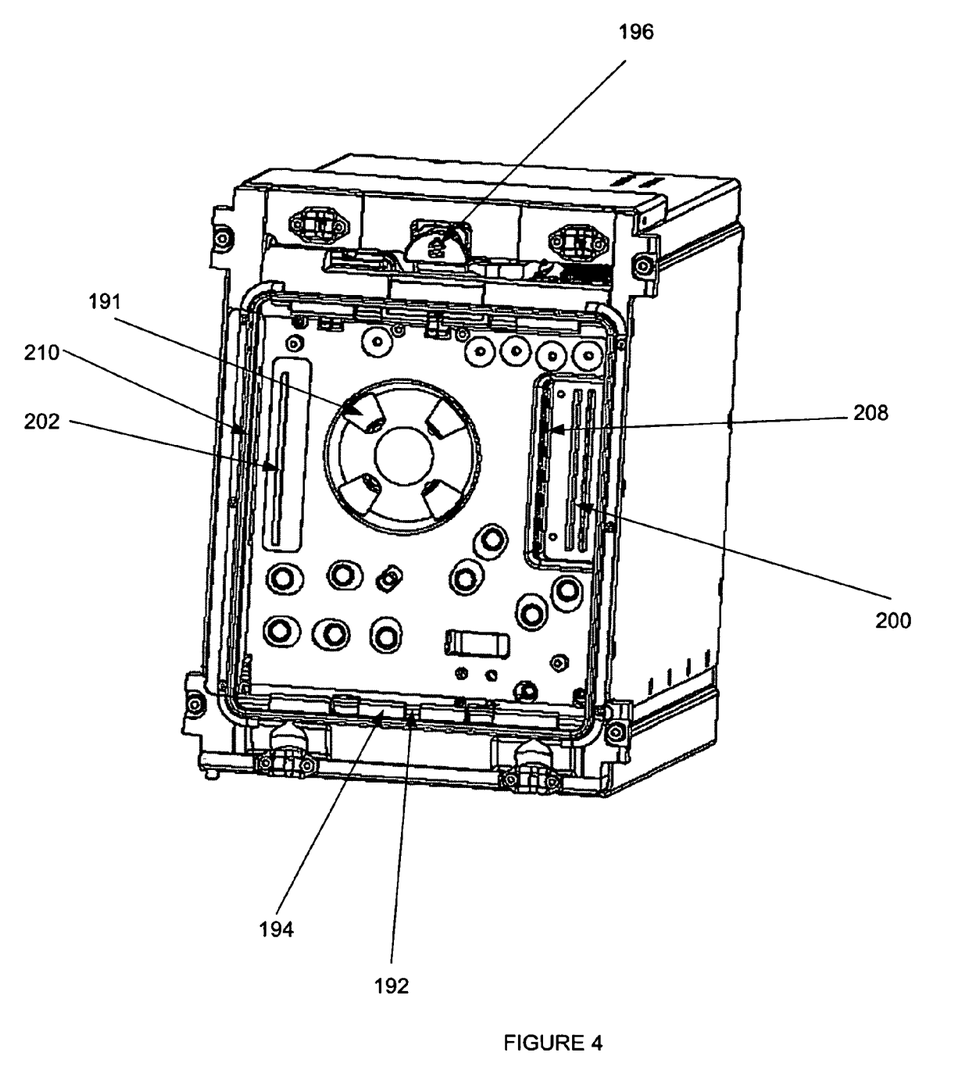
FIG. 4 is a diagrammatic representation of one embodiment of a cassette receiver in accordance with the teachings of this invention.

FIG. 4 is a diagrammatic representation of one embodiment of cassette receiver 125 without a cassette. Cassette receiver 125 can have various pneumatic input and output ports to interface with the surgical cassette. Cassette receiver 125 can further include an opening to allow peristaltic pump rollers 191 to contact the surgical cassette during operation. One embodiment of a peristaltic pump and complimentary cassette is described in U.S. patent application Ser. No. 6,293,926 to Sorensen, which is hereby fully incorporated by reference herein.

The surgical cassette, in the embodiment of FIG. 4, is held in place by a clamp having a bottom rail 192 and a top rail (not shown). Each rail can have outer clamping fingers (e.g., clamp finger 194) that contact the cassette in corresponding clamping zones and inner clamping fingers to locate the cassette during insertion and push the cassette out of cassette receiver during release. A release button 196 is pressed to initiate release of the cassette from the clamp. Cassette receiver 125 can include linear light sources to project light into the walls of the cassette chambers and sensor arrays to detect the light refracted through the chamber (or reflected from the chamber wall). Each linear light source can include a plurality of light sources vertically arranged (i.e., to project light along vertically spaced transmission paths) and positioned to project light into a wall of the cassette. For example, linear light source 200 can project light into chambers 181/182. Linear light source 200 can contain a first set of light sources aligned to project light into chamber 181 and a second set of light sources arranged at a 45 degree angle (or other angle) from the first set of light sources to project light into chamber 182. Similarly, linear light source 202 can project light into the walls of chamber 185. Respective linear sensor arrays can receive light refracted through the chamber or reflected at the chamber surface.

In this example, sensor array 206 (shown in FIG. 5) can receive light from light source 200 projected at chamber 181, a sensor array located in wall 208 can receive light from light source 200 projected at chamber 182 and a sensor array in wall 210 can receive light from light source 202. Each sensor array can include vertically arranged portions to receive light through the wall of the cassette chamber. The vertically arranged portions can be, for example, pixels, separate sensors or other mechanisms for sensing illumination.

The configuration of FIG. 4 is provided by way of example. The form factor of cassette receiver 125, placement and number of input/output ports and other features of cassette receiver 125 can depend on the surgical console 100, surgical procedure being performed or other factors as will be understood by those having ordinary skill in the art. Cassette 125 form factors having differing configurations are contemplated to be within the scope of this invention.

Figure 5:
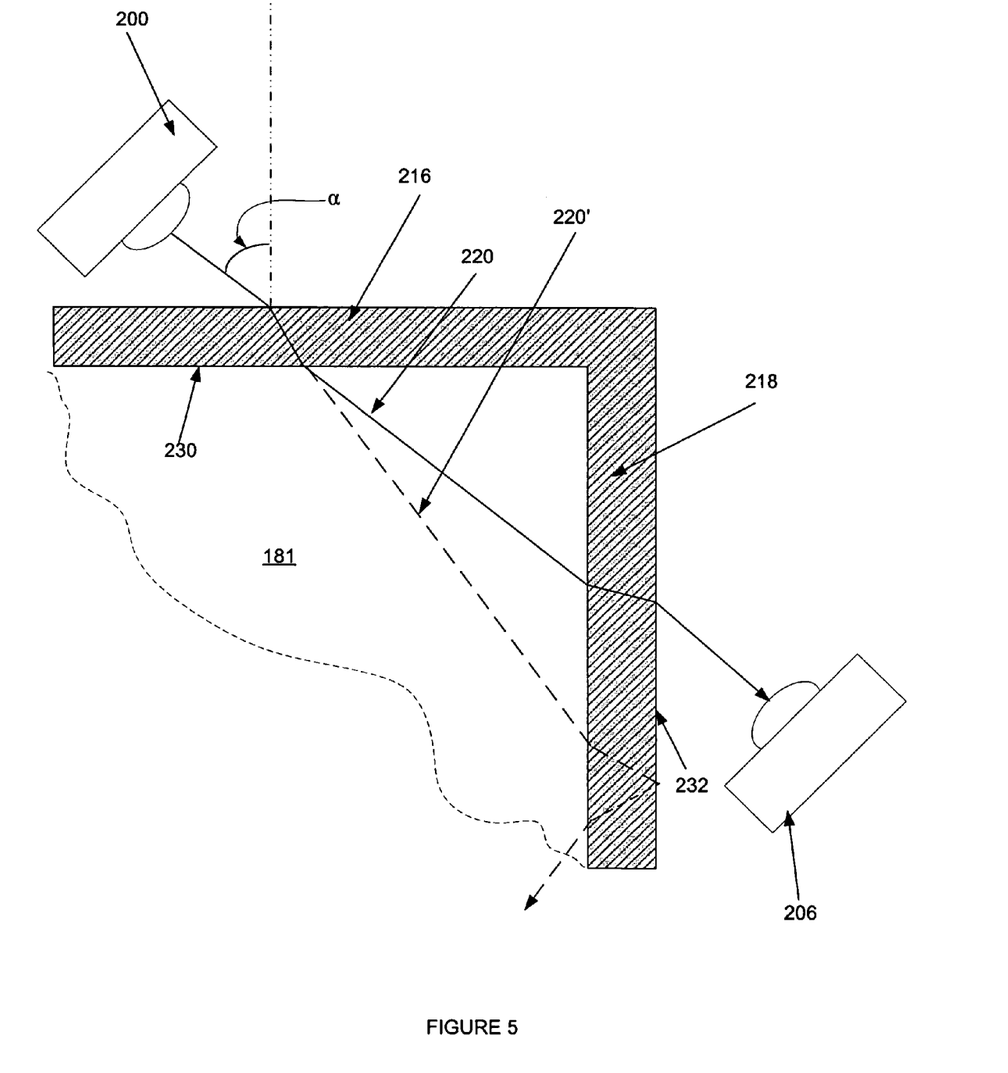
FIG. 5 is a diagrammatic representation of one embodiment of a top-view of a chamber with a linear light source and sensor array in accordance with the teachings of this invention.

FIG. 5 is a diagrammatic representation of a top view of one embodiment of a chamber 181 with light source 200 and sensor 206. Walls 216/218 of chamber 181 that face light source 200 and sensor 206, according to one embodiment, are transparent or opaque. According to one embodiment of the present invention, light source 200 can be a linear light source (i.e., a continuous light source), such as a linear LED light source, that produces light at various vertical points and sensor 206 can be a linear sensor array (i.e., a continuous sensor array), such as a linear photodiode, that detects light emitted by light source 200 at various vertical locations. One example of a linear sensor array 206 is the TAOS TSL208R linear sensor array by Texas Advanced Optoelectronic Systems of Plano, Tex., which has a resolution of 200 dots per inch (DPI). Linear light source 200 and linear sensor array 206 are connected to a circuit (not shown). According to one embodiment, linear light source 200 can also include lights to project light into another chamber (e.g., chamber 182 of FIG. 2). Preferably, the light produced by linear light source 200 provides diffuse light or parallel light beams that have a primarily horizontal transmission path.

In operation, linear light source 200 acts an emitter to emit light while linear sensor 206 acts as receiver. The angle of incidence $\alpha$ of light to chamber wall 216 can be selected so that light rays illuminate sensor 206 when passing through air in the chamber, but provide less than a threshold amount of light when passing through a fluid, such as BSS irrigating fluid, in the chamber. As an example, FIG. 4 illustrates the behavior of a light beam 220 passing through air in chamber 181 and light ray 220' passing through BSS fluid in chamber 181. In the first case, light-beam 220 penetrates wall 216, passes through the air in the top of chamber 181, through chamber wall 218 and illuminates portions of linear sensor array 206. On the other hand, light-beam 220' is refracted at surface 230 when it enters the BSS fluid (e.g., at the ABS/BSS interface). The refracted light beam 220' is further reflected at surface 232 when it reaches adjacent wall 218 to miss the pixels of sensor array 206. With an appropriate $\alpha$, the reflection at surface 232 can become total reflection because the refraction index of the cassette material (e.g. ABS plastic, acrylic or other plastic) is larger than that of air. In this case, the light is completely reflected, preventing the light beam from reaching the portions of linear sensor array 206 aligned with the BSS fluid in the chamber. Therefore, the pixels aligned with the BSS fluid will be dark. Thus, most of the light is not reflected when the transmission path of the light is intersected by the ABS/air interface but a majority of the beam (if not all) is reflected when the transmission path is intersected by the ABS/BSS interface.

The electronic circuit can compare the output of different portions of linear sensor array 206 (e.g., pixels or other sensor elements) with a threshold to determine if that portion of linear sensor array 206 is "ON" (associated with air) or "OFF" (associated with the fluid). The transition between the "ON" portion and the "OFF" portions of linear sensor array 206 marks the fluid level. It should be noted however, that other edge detection mechanisms can be employed, such as linear interpolation.

The appropriate incident angle $\alpha$ of the light is determined by the refraction index of the first fluid (e.g., air or other fluid) and the second fluid (e.g., BSS fluid or other fluid) and the cassette material (e.g., ABS plastic or other material). Preferably, $\alpha$ is chosen so that the light beam can pass through the first fluid to reach sensor array 206 but is completely reflected when it travels through the second fluid. In other embodiments in which the light beam is not totally reflected, the predetermined threshold can be set to compensate for the amount of light that does reach sensor array 206 through the second fluid. The predetermined threshold can also be adjusted to compensate for ambient light sources, light bleed from other sources and other factors that may cause a portion of sensor array 206 to output a signal in the "OFF" state.

Figure 6:
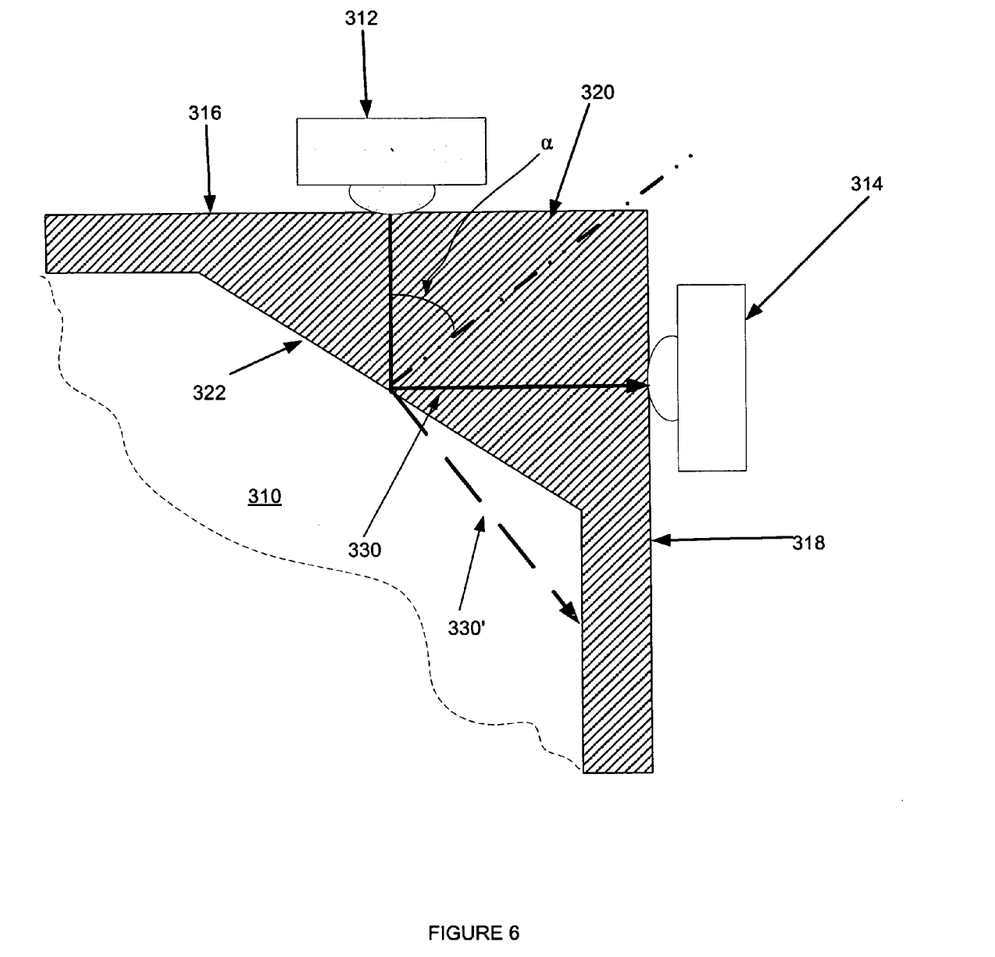
FIG. 6 is a diagrammatic representation of another embodiment of a top-view of a chamber with a linear light source and sensor array in accordance with the teachings of this invention.

FIG. 6 is a diagrammatic representation of another embodiment of a chamber 310 with light source 312 and sensor 314. Walls 316/318 of chamber 310 that face light source 312 and sensor 314, according to one embodiment, are transparent or opaque. According to one embodiment of the present invention, light source 312 can be a linear light source (i.e., a continuous light source), such as a linear LED light source, that produces light along a vertical axis and sensor 314 can be a linear sensor array (i.e., a continuous sensor array), such as a linear photodiode, that detects light emitted by light source 312 along a vertical axis. Linear light source 312 and linear sensor array 314 are connected to a circuit (not shown).

Linear light source 312 is mounted to one side of the chamber 310, illuminating chamber 310 perpendicular to wall 316. Linear sensor array 314 is mounted vertically on the adjacent side wall 318 of the chamber. Chamber 310 has a prism shaped corner 320 at the intersection of wall 316 and 318. Incident angle α can be selected so that light beams from light source 312 totally reflect from surface 322 to hit linear sensor array 314 when the light beam hits surface 322 at a point that has a first fluid on the other side (Refraction index of ABS is about 1.5, Refraction index of AIR is about 1.0), but the majority of the light beams refract at surface 322 to miss linear sensor array 314 when the light beam hits surface 322 at a point that has a second fluid on the other side (Refraction index of ABS is about 1.5, Refraction index of BSS is about 1.3). Put another way, a large portion or all the light reflects at surface 322 when the transmission path of the light is intersected by the cassette material/first fluid interface, but only a small portion of light beams is reflected if the transmission path is intersected by the cassette material/second fluid interface.

As an example, FIG. 6 illustrates the behavior of a light ray 330 primarily reflecting at the air/plastic interface at surface 322 of chamber 310 and light ray 330' primarily refracting into chamber 310 at surface 322. In the first case, light-beam 330 penetrates wall 316, passes through the plastic in corner 320, and reflects at the plastic/air interface of surface 322. On the other hand, a majority of light-beam 330' is refracted at surface 322 at the cassette material/BSS fluid interface, though some of light-beam 330' may also be reflected. In this example, the strongly reflected light (e.g., beam 330) illuminates linear sensor array 314 indicating the presence of air at that level.

Figure 7:
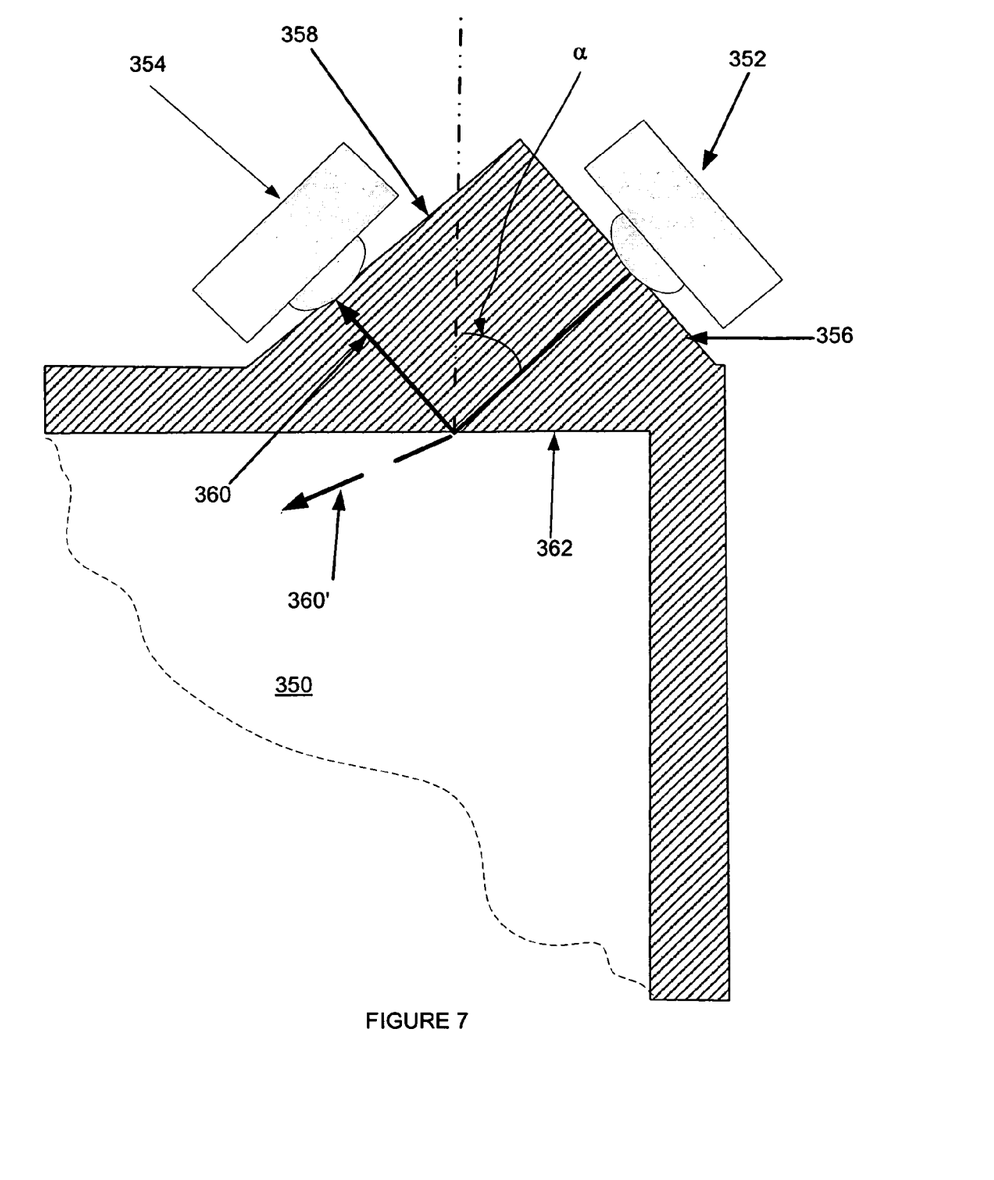
FIG. 7 is a diagrammatic representation of yet another embodiment of a top-view of a chamber with a linear light source and sensor array in accordance with the teachings of this invention.

FIG. 7 illustrates another embodiment of reflective-beam level sensing in accordance with the present invention. FIG. 7 is a diagrammatic representation of another embodiment of a chamber 350 with light source 352 and sensor 354. Walls 356/358 of the cassette that face light source 352 and sensor 354, according to one embodiment, are transparent or opaque. According to one embodiment of the present invention, light source 352 can be a linear light source (i.e., a continuous light source), such as a linear LED light source, that produces light along a vertical axis and sensor 354 can be a linear sensor array (i.e., a continuous sensor array), such as a linear photodiode, that detects light emitted by light source 352 along a vertical axis. Linear light source 352 and linear sensor array 354 are connected to a circuit (not shown).

Linear light source 352 is mounted to wall 356. Linear sensor array 354 is mounted vertically to the wall 358. The incident angle α can be selected so that light beams from light source 352 totally reflect from surface 362 to hit linear sensor array 354 when the light beam hits surface 362 at a point that has a first fluid on the other side, but refracts at surface 362 to miss linear sensor array 354 when the light beam hits surface 362 at a point that has a second fluid on the other side due to the fact that ABS has a refraction index of about 1.5, BSS has a refraction index of about 1.3 and air has a refraction index of about 1.0.

Returning to the example of an ABS cassette having chamber 350 containing air and BSS fluid, since the top of the chamber will contain the air, the upper portion of surface 362 will be an ABS/AIR interface, while the bottom portion of surface 362 will be an ABS/BSS interface. Thus, at surface 362, there are two different optical interfaces. The light beams from linear light source 352 arrive at surface 362 at an incident angle α. Part of the beam can be reflected at surface 362 and received by linear sensor array 354, while part can be refracted into chamber 350.

As an example, FIG. 7 illustrates the behavior of a light ray 360 primarily reflecting at the air/plastic interface at surface 362 of chamber 340 and light ray 360' primarily refracting into chamber 350 at surface 362. In the first case, light-beam 360 penetrates wall 356, passes through the plastic, and reflects at the plastic/air interface of surface 362. On the other hand, light-beam 360' is refracted at surface 362.

It can be noted that in the foregoing embodiments of this invention, the linear sensor array will have sufficiently illuminated pixels corresponding to air in the chamber and insufficiently illuminated pixels in the area of the chamber that includes another fluid, such as BSS. The cassette can also include features that provide for illumination of portions of the linear sensor array at a location that is a known distance below the bottom of the chamber. Referring to FIGS. 1, 3B and 4, for example, feature 187 allows light from linear light source 200 to pass to linear sensor array 206 to sufficiently illuminate corresponding portions of linear sensor array 206. Because feature 187 is a known distance d below the bottom of chamber 181, the surgical device can determine where the location of the bottom of the chamber (i.e., the zero level of the chamber).

Figure 8:
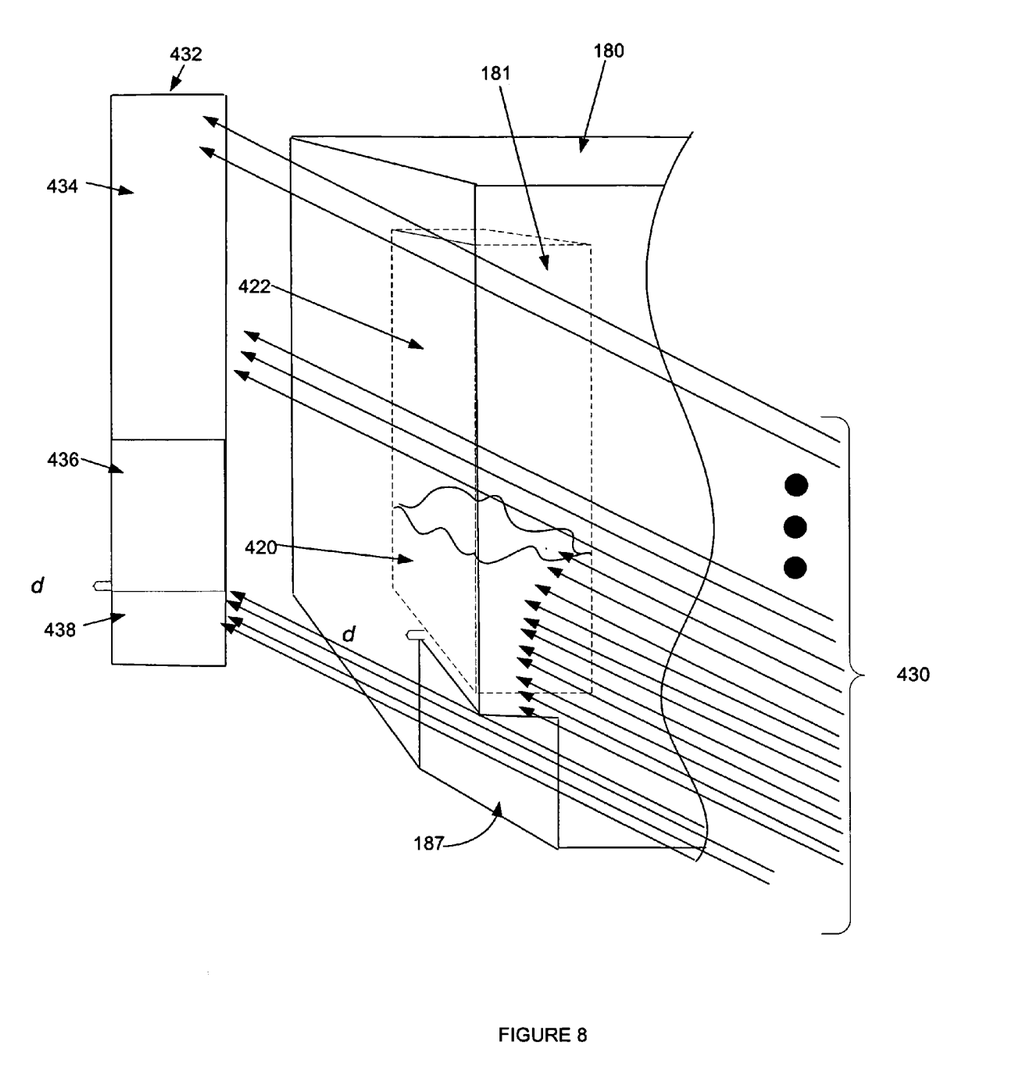
FIG. 8 is a diagrammatic representation of one embodiment of a system for determining the location of the bottom of a chamber in accordance with the teachings of this invention.

FIG. 8 is a diagrammatic representation of one embodiment of a system for determining the location of the bottom of a chamber. In this example, the bottom of chamber 181 is filled with BSS fluid 420 while the top of chamber 181 contains air 422. A linear light source projects light (represented by light rays 430). A portion of the light rays 430 passes through cutout 187 unobstructed. The light rays 430 encountering the ABS/BSS fluid interface are reflected (as discussed in conjunction with FIG. 4) to insufficiently illuminate linear sensor array 206. The light rays 430 intersected by the ABS/air interface, on the other hand, will illuminate linear sensor array 206. Thus, illumination pattern 432 can result, with area 434 illuminated by light rays passing through the air in chamber 181, area 436 insufficiently illuminated (e.g., illuminated below a threshold value) by the light rays encountering the BSS fluid in chamber 181 or solid cassette material beneath the chamber, and area 438 illuminated by the light rays passing through feature 187.

The upper level of BSS fluid 420 can be determined based on the transition between area 434 (e.g., the upper section of pixels in the "ON" state) and area 436 (e.g., pixels in the "OFF" state). The vertical location of the bottom of chamber 181 can be found based on the transition between area 436 (e.g., the pixels on the "OFF" state) and area 438 (e.g., the lower section of pixels in the "ON" state) and by adding the known distance d to the location of the edge between area 436 and area 438.

Embodiments of the present invention can thus include features, such as slots, that are closely toleranced with a direct dimension to the bottom of their respective chambers. The level sensors are occluded by the areas of the cassette below the chambers which are not slotted (or do not otherwise contain a feature to zero the chamber level). The sensors are not occluded by the slots. Since each slot is known to be a controlled distance (i.e., tightly controlled during manufacture to within the tolerances of the manufacturing process) from the bottom of its respective chamber, the location of the bottom of the chamber can be computed using the known offset between the top edge of the slot (or other feature) and the bottom of the chamber.

While, in the above embodiments, the features used to zero chambers are features that allow light to pass un-occluded to the level sensor, other features may be used. For example, in the reflective level sensing embodiments of FIGS. 6 and 7, the cassette can include an air pocket a known distance below the bottom of a chamber so that light hitting the air pocket will reflect and illuminate the sensor array just as light encountering an ABS/air interface in the chamber will. Other embodiments of the present invention can include other features that allow the location of the bottom of the cassette chamber to be determined based on an illumination pattern of a sensor array. Moreover, while the various features are shown as being directly below the corresponding chambers, the zeroing features can be located at other locations having a known distance from the bottom of the cassette chambers.

Figure 9:
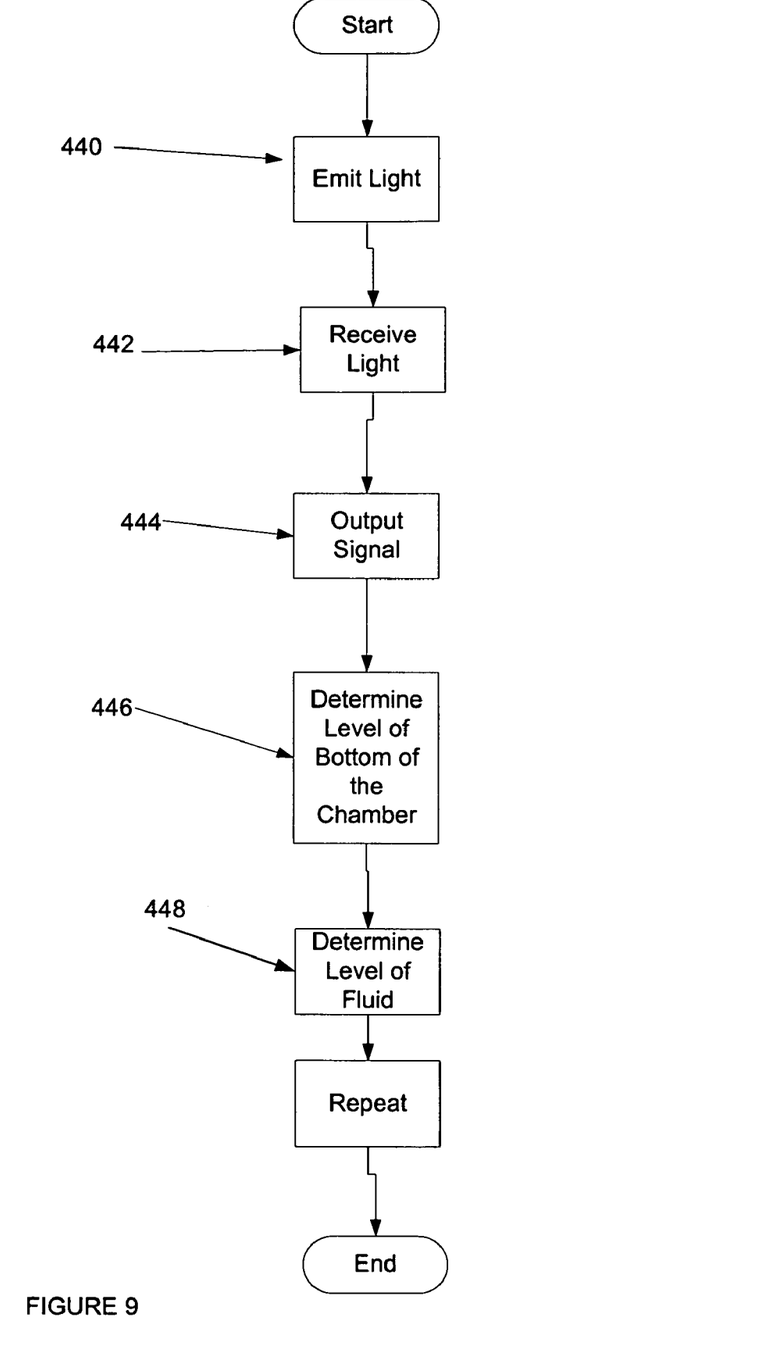
FIG. 9 is a flow chart illustrating one embodiment of a method of the present invention for level sensing.

FIG. 9 is a flow chart illustrating one embodiment of a method of this invention for calibrating a surgical console to determine the location of the bottom of a chamber. A plurality of light sources (e.g., LEDs or other light sources) projects light into the cassette containing zeroing features (step 440). The light is preferably projected light rays that are parallel. A large portion, if not all, of the light projected at the zeroing feature continues to the linear sensor array, while a much smaller amount, to none, of the light projected into an area of the cassette that is solid (or is part of the chamber containing BSS fluid) continues to the linear sensor array. The linear sensor array receives some portion of the light projected by a light source (step 442) and outputs a signal indicating the amount of light received at various portions of the sensor array (e.g., at various pixels of the array) (step 444).

At step 446, and edge detection scheme is applied to the output of the linear sensor array to determine the level of the top of the zeroing feature. According to one embodiment, the output of different portions of the linear sensor are compared with a threshold to determine if that portion of the linear sensor is in a first state. The transition between the first state and second state portions of the linear sensor array defines the edges of the zeroing feature. That is, the transition between sufficiently illuminated and insufficiently illuminated portions of the linear sensor array indicates the transition from the top of the zeroing feature (e.g., slot or other feature) to the cassette material located below the chamber. It should be noted however, other edge detection mechanisms can be employed, such as linear interpolation. The vertical location of the bottom of the chamber is calculated by adding the known distance d to the location of the top edge of the zeroing feature.

At step 448, the edge detection scheme can be further applied to the output of the linear sensor array to determine the top level of the fluid. Because the location of both the top level of the fluid and the location of the bottom of the chamber is known, the amount of fluid in the chamber is known. The steps of FIG. 9 can be repeated as needed or desired.

Figure 10:
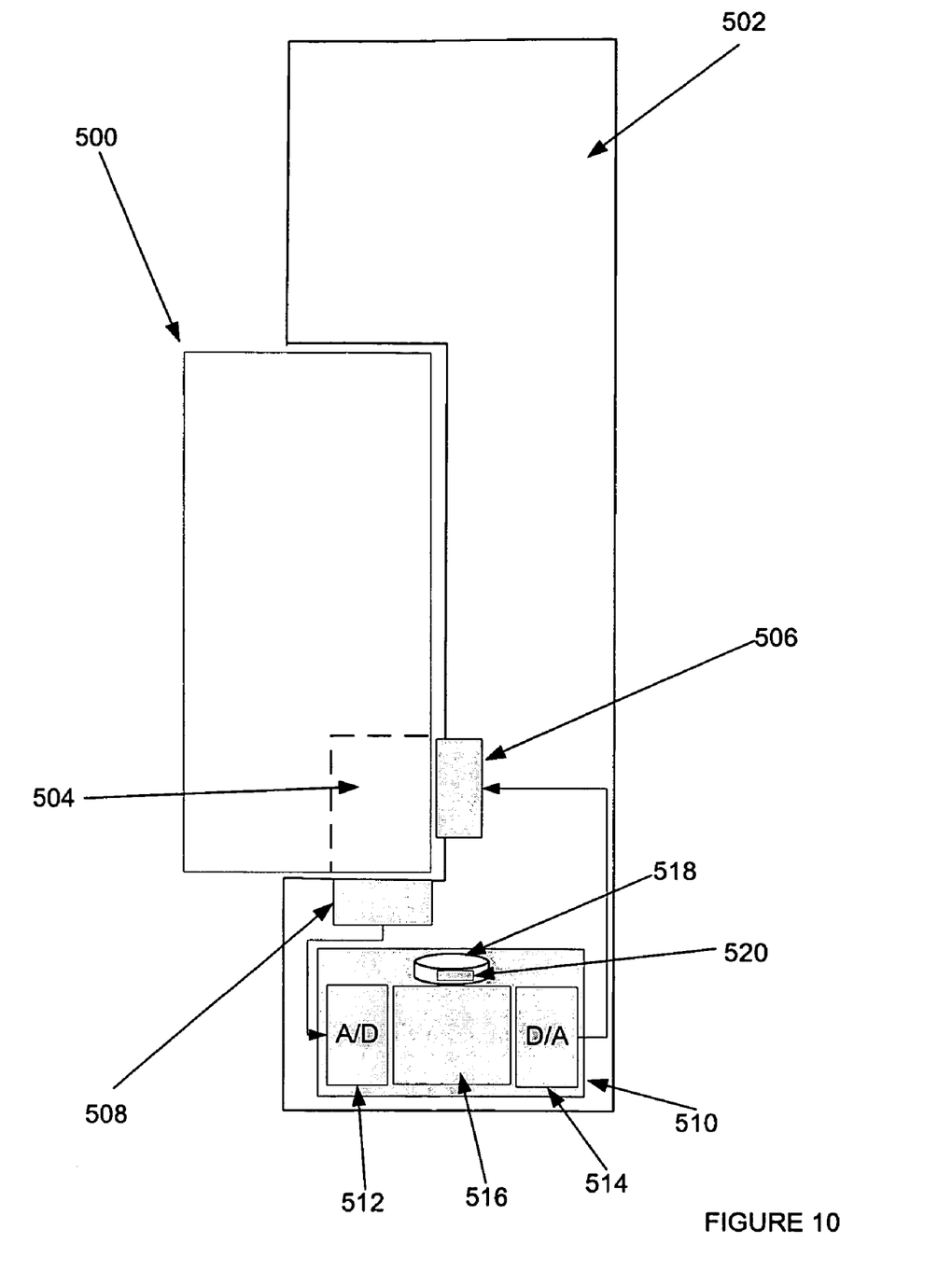
FIG. 10 is a diagrammatic representation of one embodiment of a controller in accordance with the teachings of this invention.

FIG. 10 is a schematic representation of a top view of a surgical cassette and console employing the fluid level sensor according to one embodiment of the present invention. Cassette 500 is installed in console 502. Chamber 504 is part of the cassette 500. Linear light source 506 and linear sensor array 508 are part of the console. The light source 506 projects light beam into the wall of cassette 500. The linear sensor array 508 is positioned to receive the light beam from the light source. Both the light source 506 and linear sensor array 508 are operably coupled to a controller 510.

Controller 510 can be any suitable controller known in the art including DSP, ASIC, RISK or CPU based controllers. Controller 510 can include and analog to digital (A/D) converter 512 to convert analog signals from linear sensor array 508 to digital signals. Additionally, controller 510 can include and digital to analog (D/A) converter 614 to convert digital control signals to analog signals to control the intensity of lights in light source 506. A processor 516, such as a DSP, ASIC, RISK, microcontroller or CPU or other suitable processor can access a set of instructions 520 on a computer readable memory 518. The computer readable memory can be RAM, ROM, magnetic storage, optical storage or other suitable memory and can be onboard or be accessible by processor 516. The processor 516 can execute instructions 520 to process digital inputs to determine the location of the bottom of a chamber and the level of fluid in a chamber as discussed above. Controller 510 can optionally communicate with other components of console 502 that provide additional functionality. Other embodiments of the present invention can use any suitable controller for determining the level of fluid in a chamber.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed in the following claims.

The invention claimed is:

1. A surgical cassette defining a first chamber having a first bottom surface, the surgical cassette comprising a
   a first side wall;
   a first surgical console facing wall;
   a first shaped portion to allow light projected at the surgical console facing wall of the surgical cassette to pass unobstructed past the first side wall of the cassette, wherein a first shaped portion edge is a first known distance from the first chamber bottom surface, wherein the surgical cassette defines a second chamber having a second chamber bottom surface and further comprises a second shaped portion having a second shaped portion edge a second known distance from the second chamber bottom surface;
   wherein the first shaped portion is shaped to define a slot running from the side wall to the surgical console facing wall.

2. The surgical cassette of claim 1, further comprising:
   a second side wall;
   a second surgical console facing wall; and
   wherein the second shaped portion is shaped to allow light projected at the second surgical console facing wall to pass unobstructed past the second side wall.

3. The surgical cassette of claim 1, wherein the second shaped portion is shaped to define a cutout having an upper edge the second known distance beneath the second chamber bottom surface.

4. The surgical cassette of claim 3, wherein the surgical cassette defines a third chamber having a third chamber bottom surface and further comprises:

a third shaped portion shaped to allow light to pass unobstructed, the third shaped portion having a third shaped portion edge a third known distance from the third chamber bottom surface.

5. The surgical cassette of claim 4, further comprising:
a third side wall; and
wherein the third shaped portion is shaped to allow light projected at the second surgical console facing wall to pass unobstructed past the third side wall.

6. The surgical cassette of claim 5, wherein the third shaped portion is shaped to define a second cutout the third known distance beneath the third chamber bottom surface.

7. The surgical cassette of claim 6, wherein the first, second and third known distances are equal.

8. The surgical cassette of claim 6, wherein the second and third side walls are opposite.

* * * * *